(12) United States Patent
Maruyama et al.

(10) Patent No.: US 7,514,241 B2
(45) Date of Patent: Apr. 7, 2009

(54) OLIGONUCLEOTIDE AND METHOD FOR DETECTING VEROTOXIN

(75) Inventors: Takahiro Maruyama, Yokohama (JP); Takahiko Ishiguro, Yokohama (JP); Toshiki Taya, Sagamihara (JP)

(73) Assignee: Tosoh Corporation, Shinnanyo-shi (JP)

( * ) Notice: Subject to any disclaimer, the term of this patent is extended or adjusted under 35 U.S.C. 154(b) by 281 days.

(21) Appl. No.: 11/233,094

(22) Filed: Sep. 23, 2005

(65) Prior Publication Data

US 2006/0094041 A1    May 4, 2006

Related U.S. Application Data

(63) Continuation of application No. 10/085,056, filed on Mar. 1, 2002, now abandoned.

(30) Foreign Application Priority Data

Mar. 2, 2001    (JP)    ............................. 2001-058143

(51) Int. Cl.
    *C12P 19/34*    (2006.01)
(52) U.S. Cl. .......................................... 435/91.2; 435/6
(58) Field of Classification Search ........................ None
    See application file for complete search history.

(56) References Cited

U.S. PATENT DOCUMENTS 6,136,533 A * 10/2000 Bekkaoui et al. ............... 435/6

6,162,605 A * 12/2000 Fort et al. ....................... 435/6

OTHER PUBLICATIONS

Ishiguro (Nucleic Acids Research, 1996, vol. 24, No. 24, pp. 4992-4997).*
(Buck et al (Biotechniques (1999) 27(3):528-536).*
Calderwood et al. (PNAS USA, vol. 84, p. 4364-4368).*
Gilgen et al. (Research in Microbiology (Feb. 1998) 149(2) 145-154).*
Calderwood et al. (PNAS USA vol. 84, p. 4364-4368) 1987.*
CD-ROM containing an unabridged electronic version of the article on the "Preparation and Utilization of Isolated and Purified Oligonucleotides" by Dr. Andrew Chin, dated Mar. 9, 2002.*
U.S. Appl. No. 11/313,849, filed Dec. 22, 2005, Maruyama et al.
U.S. Appl. No. 11/233,094, filed Sep. 23, 2005, Maruyama et al.
CD-ROM containing an unbridged electronic version of the article on the "Preparaion and Utilization of Isolated and Purified Oligonucleotides" by Dr. Andrew Chin.

* cited by examiner

*Primary Examiner*—Juliet C Switzer
(74) *Attorney, Agent, or Firm*—Oblon, Spivak, McClelland, Maier & Neustadt, P.C.

(57) ABSTRACT

An olignucleotide capable of binding to the intramolecular structure-free region of Verotoxin type 1 RNA or Verotoxin type 2 RNA at relatively low and constant temperature, and which can be used in a constant temperature nucleic acid amplification method, is provided. Also, a simple, speedy and highly sensitive method for detecting Verotoxin type 1 RNA or Verotoxin type 2 RNA is provided.

3 Claims, 8 Drawing Sheets

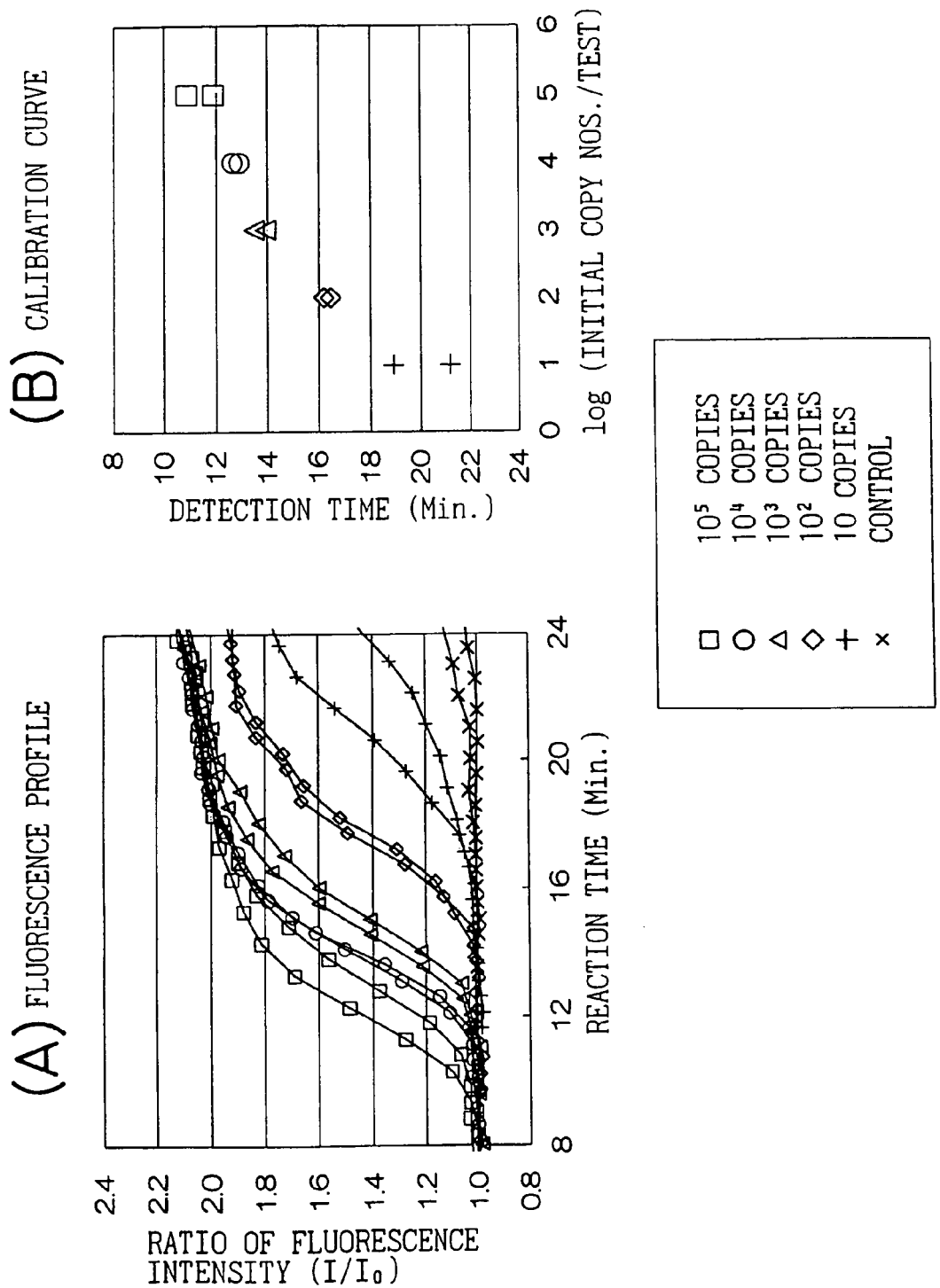

OLIGONUCLEOTIDE AND METHOD FOR DETECTING VEROTOXIN

FIELD OF THE INVENTION

The present invention relates to oligonucleotides for use in detecting Verotoxin (hereafter, abbreviated as "VT") in clinical examinations, public health examinations, food evaluations and food poisoning examinations, as well as a detection method using said oligonucleotides. The oligonucleotide provided by the present invention can be used as a gene diagnosing reagent for cleaving, amplifying and detecting RNA or DNA, and is, for example, useful as a reagent for quantifying or diagnosing VT.

PRIOR ART

Verotoxin is a potent toxin produced by Verotoxin-producing *Escherichia coli* (hereafter, abbreviated as "VTEC"), typically pathogenic *E. coli* O157. Although the primary symptom caused by infection with VTEC can be food poisoning represented by hemorrhagic colitis, it is reported that, in some cases, the symptom will advance to a hemolytic uremic syndrome (HUS) and, at worst, it will cause death.

Although VTEC has many various serotypes, which may be 60 types or more, in view of their detection frequencies, it is deemed that the major serotype is O157:H7. Further, VT includes VT type 1 which has the same structure as Shiga toxin produced by *Shigella dysenteriae* as well as VT type 2 having different physicochemical and immunological properties.

In Japan, VTEC mass infection occurs frequently and, therefore, in order to accomplish early detection and exclusion of the infectious source, speedy detection is desired. Further, from a clinical standpoint, since it is demonstrated that dosing with antibacterial composition comprising antibiotics at an early condition stage, i.e. within a few days from the onset of the disease is effective, speedy identification of the bacteria is becoming important.

Means which had been used for examining VT include detection of O157 antigen. However, it is known that some *Salmonella* and *Citrobacter* strains show cross-antigenecity with O157 antigen, and it is reported that this detection method sometimes provides false positive results. In addition, mass infections caused by serotypes other than O157 have been reported, and therefore it is required to carry out tests using antisera against various serotypes.

Recently, a method of selectively detecting Verotoxin-producing bacteria comprising construction of oligonucleotides that selectively hybridize against a VTEC gene, and use of these oligonucleotides in a gene-amplification process (PCR process) as primers, has been proposed. However, since identification of the amplified DNA fragment is carried out with agarose electrophoresis, there remains a problem in view of the lack of speeds.

Contrary to the other types of food poisoning, VT results in a great deal of harm with smaller amounts of contaminating bacteria and, therefore, the food examination field, and the like, desire a more rapid and highly sensitive detection method. However, previous methods carry problems regarding their speed and simplicity. In addition, in order to simplify the an examination, an examining instrument which carries out the detection automatically is desired.

It is known that when the target nucleic acid is RNA, Reverse Transcription-Polymerase Chain Reaction (RT-PCR) can be used. This method involves synthesizing a cDNA from the target RNA in a reverse transcription step, and then amplifying a specific sequence of said CDNA by repetition of a cycle comprising heat denaturation, primer annealing and extension reactions, in the presence of a pair of primers complementarily and homologous to both ends of said specific sequence (the antisense primer may be the same as the one used in reverse transcription step) as well as a thermostable DNA polymerase. However, RT-PCR method requires a two-step operation (a reverse transcription step and a PCR step) as well as an operation involving repetition of rapidly increasing and decreasing the temperature, which prevent its automation.

As amplification methods in cases where the target nucleic acid is RNA, in addition to the above, NASBA and 3SR method are known, whereby the specific sequence is amplified by the concerted action of a reverse transcriptase and an RNA polymerase. In these methods, the following procedures are carried out: using the target RNA as a template, a double-stranded DNA including a promoter sequence is synthesized with a primer containing the promoter sequence, reverse transcriptase and Ribonuclease H; this double-stranded DNA is used as a template in synthesizing an RNA containing the specific sequence with an RNA polymerase and, subsequently, this RNA provides a template in a chain reaction for synthesizing a double-stranded DNA containing the promoter sequence.

NASBA, 3SR, and the like, allow amplification at a constant temperature and are considered suitable for automation.

Because amplification methods such as NASBA and 3SR methods involve relatively low temperature reactions (41° C., for example), however, the target RNA may form an intramolecular structure that inhibits binding of the primer, which may reduce the reaction efficiency. Therefore, they require subjecting the target RNA to heat denaturation prior to the amplification reaction so as to destroy the intramolecular structure thereof and thus to improve the primer binding efficiency. As a result, the simplicity and speed of the methods are impaired.

Thus, an object of the present invention is to provide an oligonucleotide capable of complementarily binding to an intramolecular structure-free region of the target RNA, the binding of which against the target RNA would not be inhibited even when being manipulated at relatively low temperature (for example, between 35 and 50° C., preferably, about 41° C.), whereby its reaction efficiency would not be impaired. In particular, an object of the present invention is to provide an oligonucleotide capable of binding to the intramolecular structure-free region of VT1 RNA or VT2 RNA at relatively low temperature, or to provide an oligonucleotide primer which can be used in a nucleic acid amplification method so as to detect VT1 RNA or VT2 RNA, and also to provide simple, speedy and highly sensitive detecting method using such an oligonucleotide.

The invention according to embodiment 1 and intended to accomplish the objects relates to an oligonucleotide for detection or amplification of VT1 RNA, which oligonucleotide is capable of specifically binding to VT1 RNA, and comprises at least 10 contiguous bases of any of the sequences listed as SEQ. ID. Nos. 1 to 5.

Moreover, the invention according to embodiment 2 and intended to accomplish the objects relates to an oligonucleotide for detection or amplification of VT2 RNA, which oligonucleotide is capable of specifically binding to VT2 RNA, and comprises at least 10 contiguous bases of any of the sequences listed as SEQ. ID. Nos. 6 to 14.

Furthermore, the invention according to embodiment 3 and intended to accomplish the objects relates to a process of detecting VT1 RNA, wherein a specific sequence of VT1

RNA present in a sample is used as a template for synthesis of a cDNA employing an RNA-dependent DNA polymerase, the RNA of the formed RNA/DNA hybrid is digested by ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA-polymerase, the double-stranded DNA produces an RNA transcription product in the presence of an RNA polymerase, and the RNA transcription product is then used as a template for cDNA synthesis employing the RNA-dependent DNA polymerase, the amplification process being characterized by employing a first oligonucleotide capable of specifically binding to VT1 RNA and comprising at least 10 contiguous bases of any of the sequences listed as SEQ. ID. Nos. 1 to 5 and a second oligonucleotide comprising at least 10 contiguous bases of any of the sequences listed as SEQ. ID. Nos. 15 to 18, where either the first or second oligonucleotide includes the RNA polymerase promoter sequence at the 5' end.

Still furthermore, the invention according to embodiment 4 and intended to accomplish the objects relates to a process of detecting VT2 RNA, wherein a specific sequence of VT2 RNA present in a sample is used as a template for synthesis of a cDNA employing an RNA-dependent DNA polymerase, the RNA of the formed RNA/DNA hybrid is digested by ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA polymerase, the double-stranded DNA produces an RNA transcription product in the presence of an RNA polymerase, and the RNA transcription product is then used as a template for cDNA synthesis employing the RNA-dependent DNA polymerase, the amplification process being characterized by employing a first oligonucleotide capable of specifically binding to VT2 RNA, and comprising at least 10 contiguous bases of any of the sequences listed as SEQ. ID. Nos. 6 to 14 and a second oligonucleotide comprising at least 10 contiguous bases of any of the sequences listed as SEQ. ID. Nos. 19 to 23, where either the first or second oligonucleotide includes the RNA polymerase promoter sequence at the 5' end.

The invention according to embodiment 5 relates to the process according to embodiment 3 or 4, wherein said amplification is carried out in the presence of an oligonucleotide probe capable of specifically binding to the RNA transcription product resulting from the amplification and labeled with an intercalator fluorescent pigment, and measuring changes in the fluorescent properties of the reaction solution. The invention according to embodiment 6 relates to the process according to embodiment 5, characterized in that the oligonucleotide probe is designed so as to complementarily bind to at least a portion of the sequence of the RNA transcription product, and the fluorescent property changes relative to that of a situation where a complex formation is absent. The invention according to embodiment 7 relates to the process according to embodiment 5 for detecting VT1 RNA, characterized in that the oligonucleotide probe comprises at least 10 contiguous bases of SEQ. ID. No. 24 or its complementary sequence. The invention according to embodiment 8 relates to the process according to embodiment 5 for detecting VT2 RNA, characterized in that the oligonucleotide probe comprises at least 10 contiguous bases of SEQ. ID. No. 25 or its complementary sequence. The present invention will be explained below.

First, the present invention provides an oligonucleotide useful in detecting VT1 RNA, which oligonucleotide is capable of specifically binding to VT1 RNA, and comprises at least 10 contiguous bases of any of the sequence listed as SEQ. ID. Nos. 1 to 5. This oligonucleotide is capable of binding to VT1 RNA at relatively low and constant temperature (35 to 50° C., preferably, about 41° C.).

The RNA detecting process involving the step of amplifying VT1 RNA in a sample provided by the present invention includes PCR method, NASBA method, 3SR method, or the like. However, it is preferred that the nucleic acid amplification is a one which can be conducted under constant temperature, such as NASBA or 3SR method in which specific sequence within VT1 RNA is amplified with the concerted action of reverse transcriptase and RNA polymerase.

For example, in the NASBA method, a specific sequence of VT1 RNA present in a sample is used as a template for synthesis of a cDNA employing an RNA-dependent DNA polymerase, the RNA of the RNA/DNA hybrid is digested by ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA polymerase, the double-stranded DNA produces an RNA transcription product in the presence of an RNA polymerase, and the RNA transcription product is then used as a template for cDNA synthesis employing the RNA-dependent DNA polymerase. The process of the present invention is characterized by employing a first oligonucleotide capable of specifically binding to VT1 RNA and comprising at least 10 contiguous bases of any of the sequences listed as SEQ. ID. Nos. 1 to 5 and a second oligonucleotide comprising at least 10 contiguous bases of any of the sequences listed as SEQ. ID. Nos. 15 to 18 and having a sequence homologous to a portion of the VT1 RNA sequence to be amplified, where either the first or second oligonucleotide includes the RNA polymerase promoter sequence at the 5' end.

Although the RNA-dependent DNA polymerase, the DNA-dependent DNA polymerase and the ribonuclease H are not critical, AMV reverse transcriptase that has all of these types of activity is most preferably used. Moreover, although the RNA polymerase is not critical, T7 phage RNA polymerase or SP6 phage RNA polymerase is preferably used.

In the above amplification process, an oligonucleotide that is complementary to the region adjacent to and overlapping with the 5' end region of the specific sequence (bases 1 to 10) of VT1 RNA sequence is added, and the VT1 RNA is cleaved (with ribonuclease H) at the 5' end region of the specific sequence to provide the initial template for nucleic acid amplification, thereby allowing amplification of VT1 RNA even when the specific sequence is not positioned at the 5' end. The oligonucleotide used for this cleaving may, for example, be any of those of SEQ. ID. Nos. 1 to 5, provided that it differs from the one used as the first oligonucleotide in the amplification process. In addition, the oligonucleotide for cleaving is preferably chemically modified (for example, aminated) at the 3' hydroxyl group in order to prevent an extension reaction from the 3' end.

Although the RNA transcription product obtained by the above nucleic acid amplification can be detected by a known method, per se, preferably, it is detected by carrying out the above amplification process in the presence of an oligonucleotide probe labeled with an intercalator fluorescent pigment, and measuring changes in the fluorescent properties of the reaction solution. Examples of the oligonucleotide probe include one in which the intercalator fluorescent pigment is bonded to a phosphorus atom in the oligonucleotide through a linker. The probe is characterized in that when it forms a double-stranded chain with the target nucleic acid (complementary nucleic acid), separation analysis is not required because the intercalator portion intercalates into the double-stranded chain portion to vary the fluorescent characteristics (Ishiguro, T. et al. (1996), Nucleic Acids Res. 24 (24) 4992-4997).

The probe sequence is not critical so long as it has a sequence complementary to at least a portion of the RNA transcription product. However, the probe sequence is preferably one comprising at least 10 contiguous bases of the sequence listed as SEQ. ID. No. 24. Moreover, chemical modification (for example, glycolic acid addition) at the 3' end hydroxyl group of the probe is preferred in order to inhibit an extension reaction in which the probe acts as a primer.

It becomes possible to amplify and detect RNA comprising the same sequence as the specific sequence of VT1 RNA in a single tube at a constant temperature and in a single step by carrying out the amplification process in the presence of the probe, as explained above, and, thus, the amplification process is easily automated.

Next, the present invention provides an oligonucleotide useful in detecting VT2 RNA, which oligonucleotide is capable of specifically binding to VT2 RNA, and comprises at least 10 contiguous bases of any of the sequence listed as SEQ. ID. Nos. 6 to 14. This oligonucleotide is capable of binding to VT2 RNA at relatively low and constant temperature (35 to 50° C., preferably, about 41° C.).

The RNA detecting process involving the step of amplifying VT2 RNA in a sample provided by the present invention includes PCR method, NASBA method, 3SR method, or the like. However, it is preferred that the nucleic acid amplification is a one which can be conducted under constant temperature, such as NASBA or 3SR method in which specific sequence within VT2 RNA is amplified with the concerted action of reverse transcriptase and RNA polymerase.

For example, in the NASBA method, a specific sequence of VT2 RNA present in a sample is used as a template for synthesis of a cDNA employing an RNA-dependent DNA polymerase, the RNA of the RNA/DNA hybrid is digested by ribonuclease H to produce a single-stranded DNA, the single-stranded DNA is then used as a template for production of a double-stranded DNA having a promoter sequence capable of transcribing RNA comprising the specific sequence or the sequence complementary to the specific sequence employing a DNA-dependent DNA polymerase, the double-stranded DNA produces an RNA transcription product in the presence of an RNA polymerase, and the RNA transcription product is then used as a template for cDNA synthesis employing the RNA-dependent DNA polymerase. The process of the present invention is characterized by employing a first oligonucleotide capable of specifically binding to VT2 RNA and comprising at least 10 contiguous bases of any of the sequences listed as SEQ. ID. Nos. 6 to 14 and a second oligonucleotide comprising at least 10 contiguous bases of any of the sequences listed as SEQ. ID. Nos. 19 to 23 and having a sequence homologous to a portion of the VT2 RNA sequence to be amplified, where either the first or second oligonucleotide includes the RNA polymerase promoter sequence at the 5' end.

Although the RNA-dependent DNA polymerase, the DNA-dependent DNA polymerase and the ribonuclease H are not critical, AMV reverse transcriptase that has all of these types of activity is most preferably used. Moreover, although the RNA polymerase is not critical, T7 phage RNA polymerase or SP6 phage RNA polymerase is preferably used.

In the above amplification process, an oligonucleotide that is complementary to the region adjacent to and overlapping with the 5' end region of the specific sequence (bases 1 to 10) of VT2 RNA sequence is added, and the VT2 RNA is cleaved (with ribonuclease H) at the 5' end region of the specific sequence to give the initial template for nucleic acid amplification, thereby allowing amplification of VT2 RNA even when the specific sequence is not positioned at the 5' end. The oligonucleotide used for this cleaving may, for example, be any of those of SEQ. ID. Nos. 6 to 14, provided that it differs from the one used as the first oligonucleotide in the amplification process. In addition, the oligonucleotide for cleaving is preferably chemically modified (for example, aminated) at the 3' hydroxyl group in order to prevent an extension reaction from the 3' end.

Although the RNA transcription product obtained by the above nucleic acid amplification can be detected by a method known per se, preferably, it is detected by carrying out the above amplification process in the presence of an oligonucleotide probe labeled with an intercalator fluorescent pigment, and measuring changes in the fluorescent properties of the reaction solution. Examples of the oligonucleotide probe include one in which the intercalator fluorescent pigment is bonded to a phosphorus atom in the oligonucleotide through a linker. The probe is characterized in that when it forms a double-stranded chain with the target nucleic acid (complementary nucleic acid), separation analysis is not required because the intercalator portion intercalates into the double-stranded chain portion to vary the fluorescent characteristics (Ishiguro, T. et al. (1996), Nucleic Acids Res. 24 (24) 4992-4997).

The probe sequence is not critical so long as it has a sequence complementary to at least a portion of the RNA transcription product. However, the probe sequence is preferably one comprising at least 10 contiguous bases of the sequence listed as SEQ. ID. No. 25. Moreover, chemical modification (for example, glycolic acid addition) at the 3' end hydroxyl group of the probe is preferred in order to inhibit an extension reaction based on the probe used as a primer.

It becomes possible to amplify and detect RNA comprising the same sequence as the specific sequence of VT2 RNA in a single tube at a constant temperature and in a single step by carrying out the amplification process in the presence of the probe, as explained above, and, thus, the amplification process is easily automated.

BRIEF DESCRIPTION OF THE DRAWINGS

FIG. 8 shows the results obtained in Example 5 for samples prepared from the VT2 RNA standard with an initial RNA amount of from $10_1$ copies/30 µl to $10_3$ copies/30 µl. Panel (a) is a fluorescence profile exhibiting the fluorescence increase ratio that increases with the reaction time-course formation of RNA. Panel (b) is a calibration curve exhibiting the relationship between the logarithm of the initial RNA amount and the detection time (time at which the relative fluorescence reaches 1.2). □ shows the result for $10_5$ copies, ○ is for $10_4$ copies, Δ is for $10_3$ copies, ◇ is for $10_2$ copies, + is for 10 copies, and × is for control. It was demonstrated that RNA with initial copies of $10_1$ copies/30 µl can be detected by a reaction for about 20 minutes, and that there is a correlation between the initial RNA amount and the detection time.

EXAMPLES

Figure 1:
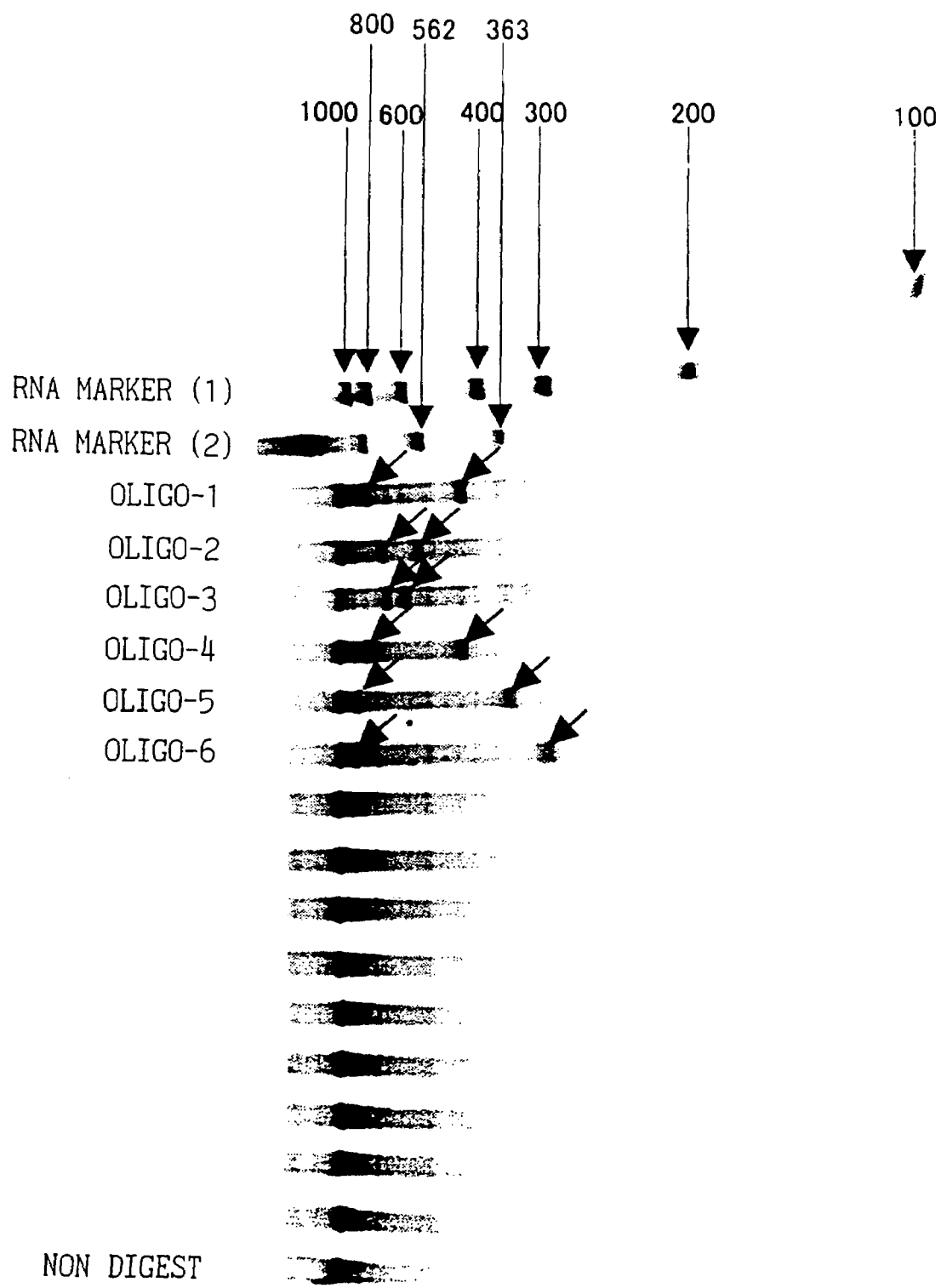
FIG. 1 is a urea modified 6% polyacrylamide electrophoresis diagram for samples obtained by performing cleaving experiments on VT1 RNA standard at 41° C., using Oligos 1 to 6 and AMV-Reverse Transcriptase (black and white inverted). The lanes without any indications are unrelated to the present invention.

The present invention will now be explained in greater detail by way of examples, with the understanding that the invention is not limited by these examples.

Example 1

(1) An oligonucleotide which specifically binds to VT1 RNA at 41° C. was selected. A standard RNA comprising a region of base Nos. 228 to 1558 of the VT1 RNA base sequence (Calderwood, S. B. et al., Proc. Natl. Acad. Sci. U.S.A., 84, 4364-4368 (1987), US GenBank Registered No. M16625) was quantified by ultraviolet absorption at 260 nm, and then diluted to a concentration of 1.33 pmol/µl with an RNA diluent (10 mM Tris-HCl (pH 8.0)), 0.1 mM EDTA, 1 mM DTT, 0.5 U/µl RNase Inhibitor).

(2) 14.0 µl of a reaction solution having the following composition was dispended into 0.5 ml volume PCR tubes (Gene Amp Thin-Walled Reaction Tube™, Perkin-Elmer Co. Ltd.)

Reaction Solution Composition
60.0 mM Tris-HCl buffer (pH 8.6)
90.0 mM potassium chloride
13.0 mM magnesium chloride
1.0 mM DTT
80.0 nM standard RNA
0.8 µM oligonucleotide (one of the oligonucleotides shown below).
Oligo-1: SEQ. ID. No. 1;
Oligo-2: SEQ. ID. No. 2;

Oligo-3: SEQ. ID. No. 26;
Oligo-4: SEQ. ID. No. 3;
Oligo-5: SEQ. ID. No. 4;
Oligo-6: SEQ. ID. No. 5
Distilled water for adjusting volume (3) The reaction solutions were then incubated at 41° C. for 5 minutes, and then 1 µl of 8.0 U/µl AMV-Reverse Transcriptase (Takara Shuzo Co. Ltd.; an enzyme which cleaves RNA of a double stranded-DNA/RNA) was added thereto.

(4) Subsequently, the PCR tubes were incubated at 41° C. for 10 minutes. Modified-urea polyacrylamide gel (acrylamide concentration: 6%; urea: 7M) electrophoresis was conducted to confirm the cleaved fragments after the reaction. Dyeing following the electrophoresis was carried out with SYBR Green II™ (Takara Shuzo Co. Ltd.). Upon binding of the oligonucleotide to the specific site of the target RNA, RNA of the double stranded DNA/RNA is cleaved by the ribonuclease H activity of AMV-Reverse Transcriptase and, thereby, a characteristic band can be observed.

(5) The results of the electrophoresis are shown in FIG. 1 (black and white inverted). If the oligonucleotide binds specifically to the standard RNA, the standard RNA will be cleaved at this region, yielding a decomposition product having a characteristic chain length. Table 1 shows the positions of the standard RNA where each oligonucleotide had specifically bind and the expected band lengths of the fragments. Cleavages at the expected positions were confirmed with Oligos 1 to 6. These indicated that these oligonucleotides bind strongly to the VT1 RNA under a constant temperature of 41° C.

TABLE 1

| Oligo | Position[1] | Expected band Length (base) |
|---|---|---|
| Oligo -1 | 425 | 425, 912 |
| Oligo -2 | 555 | 555, 782 |
| Oligo -3 | 710 | 710, 627 |
| Oligo -4 | 890 | 890, 447 |
| Oligo -5 | 980 | 980, 357 |
| Oligo -6 | 1031 | 1031, 306 |

[1]The position designates the 5' end number of the oligonucleotide which binds to the VT1 RNA standard (1337 base).

Example 2

(1) An oligonucleotide which specifically binds to VT2 RNA at 41° C. was selected. A standard RNA comprising a region of base Nos. 81 to 1437 of the VT2 RNA base sequence (Schmitt, C. K. et al., Infect. Immun, 59, 1065-1073 (1991), US GenBank Registered No. X07865) was quantified by ultraviolet absorption at 260 nm, and then diluted to a concentration of 1.75 pmol/µl with an RNA diluent (10 mM Tris-HCl (pH 8.0)), 0.1 mM EDTA, 1 mM DTT, 0.5 U/µl RNase Inhibitor).

(2) 14.0 µl of a reaction solution having the following composition was dispended into 0.5 ml volume PCR tubes (Gene Amp Thin-Walled Reaction Tube™, Perkin-Elmer Co. Ltd.)
Reaction Solution Composition
60.0 mM Tris-HCl buffer (pH 8.6)
90.0 mM potassium chloride
13.0 mM magnesium chloride
1.0 mM DTT
80.0 nM standard RNA
0.8 µM oligonucleotide (one of the oligonucleotides shown below).

Oligo-7: SEQ. ID. No. 6;
Oligo-8: SEQ. ID. No. 7;
Oligo-9: SEQ. ID. No. 8;
Oligo-10: SEQ. ID. No. 9;
Oligo-11: SEQ. ID. No. 10;
Oligo-12: SEQ. ID. No. 11;
Oligo-13: SEQ. ID. No. 12;
Oligo-14: SEQ. ID. No. 13;
Oligo-15: SEQ. ID. No. 14;
Distilled water for adjusting volume (3) The reaction solutions were then incubated at 41° C. for 5 minutes, and then 1 µl of 8.0 U/µl AMV-Reverse Transcriptase (Takara Shuzo Co. Ltd.; an enzyme which cleaves RNA of a double stranded-DNA/RNA) was added thereto.

(4) Subsequently, the PCR tubes were incubated at 41° C. for 10 minutes. Modified-urea polyacrylamide gel (acrylamide concentration: 6%; urea: 7M) electrophoresis was conducted to confirm the cleaved fragments after the reaction. Dyeing following the electrophoresis was carried out with SYBR Green II™ (Takara Shuzo Co. Ltd.). Upon binding of the oligonucleotide to the specific site of the target RNA, RNA of the double stranded DNA/RNA is cleaved by the ribonuclease H activity of AMV-Reverse Transcriptase and, thereby, a characteristic band can be observed.

Figure 2:
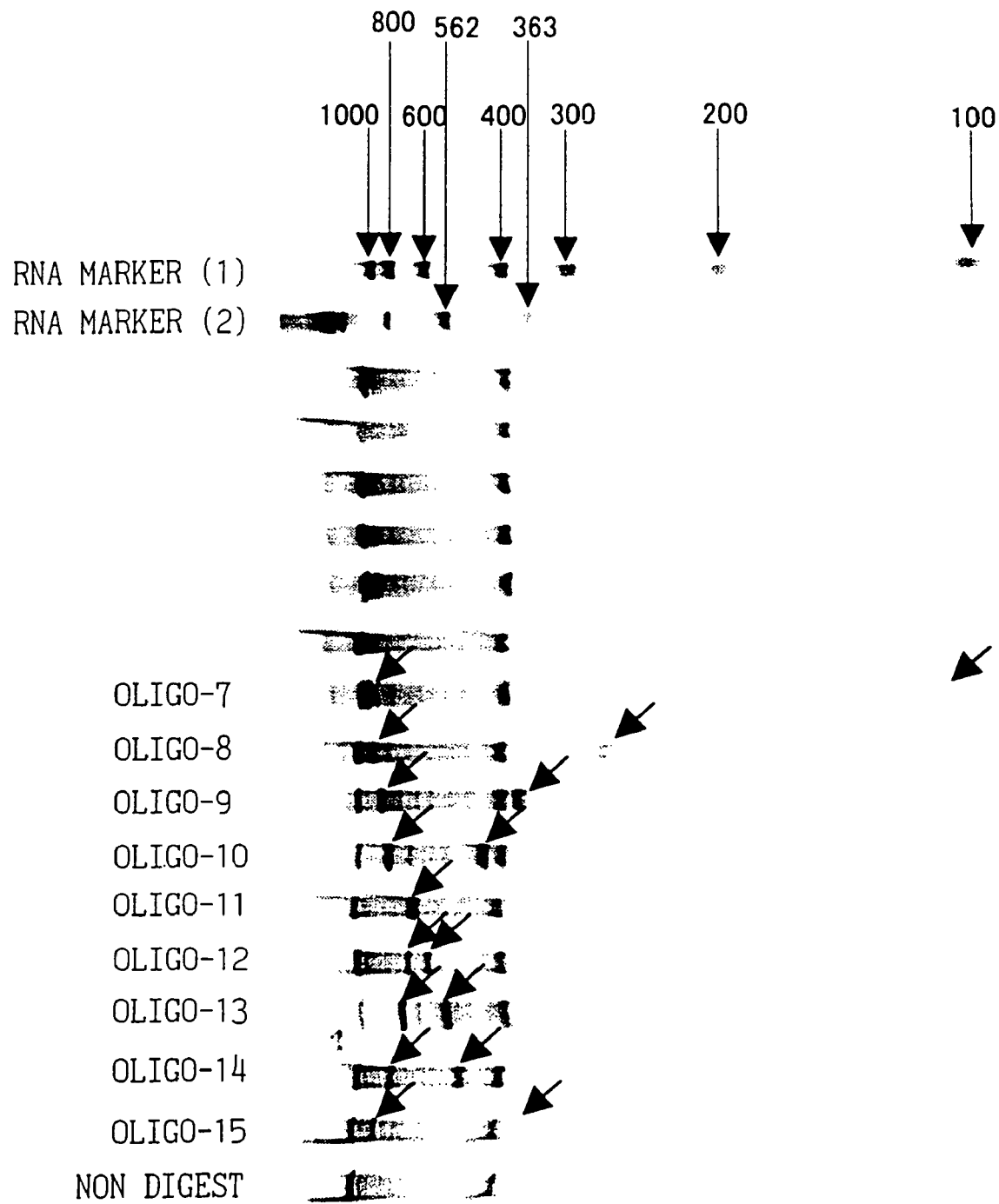
FIG. 2 is a urea modified 6% polyacrylamide electrophoresis diagram for samples detained by performing cleaving experiments on VT2 RNA standard at 41° C., using Oligos 7 to 15 and AMV-Reverse Transcriptase (black and white inverted). The lanes without any indications are unrelated to the present invention.

(5) The results of the electrophoresis are shown in FIG. 2 (black and white inverted). If the oligonucleotide binds specifically to the standard RNA, the standard RNA will be cleaved at this region, yielding a decomposition product having a characteristic chain length. Table 2 shows the positions of the standard RNA where each oligonucleotide had specifically bound and the expected band lengths of the fragments. Cleavages at the expected positions were confirmed with Oligos 7 to 15. These indicated that these oligonucleotides bind strongly to the VT2 RNA under a constant temperature of 41° C.

TABLE 2

| Oligo | Position[1] | Expected band Length (base) |
|---|---|---|
| Oligo -7 | 102 | 102, 1259 |
| Oligo -8 | 260 | 260, 1101 |
| Oligo -9 | 365 | 365, 996 |
| Oligo -10 | 436 | 436, 925 |
| Oligo -11 | 675 | 675, 686 |
| Oligo -12 | 723 | 723, 638 |
| Oligo -13 | 787 | 787, 574 |
| Oligo -14 | 848 | 848, 513 |
| Oligo -15 | 986 | 986, 375 |

[1]The position designates the 5' end number of the oligonucleotide which binds to the VT2 RNA standard (1361 base).

Example 3

RNA amplification reactions were carried out using the oligonucleotides which specifically bind to VT1 RNA.

(1) As described in example 1, VT1 standard RNA was diluted to $10_4$ copies/2.5 µl and $10_3$ copies/2.5 µl with an RNA diluent (10 mM Tris-HCl (pH 8.0), 1 mM EDTA, 0.5 U/µl RNase Inhibitor (Takara Shuzo Co. Ltd.), 5 mM DTT). In the control test sections (negative), only the diluent was used.

(2) 23.3 µl of a solution having the following composition was dispended into 0.5 ml volume PCR tubes (Gene Amp Thin-Walled Reaction Tube™, Perkin-Elmer Co. Ltd.), followed by addition of 2.5 µl of the above RNA sample.

Reaction Solution Composition (each concentration represents a concentration in a final reaction solution volume of 30 μl)

60 mM Tris-HCl buffer (pH 8.6)
    17 mM magnesium chloride
    90 mM potassium chloride
    39 U RNase Inhibitor
    1 mM DTT
    0.25 μl of each dATP, dCTP, dGTP, dTTP
    3.6 mM ITP
    3.0 μl of each ATP, CTP, GTP, UTP
    0.16 μM cleavage oligonucleotide
    1.0 μM second oligonucleotide
    1.0 μM first oligonucleotide
    13% DMSO
    Distilled water for adjusting volume (3) RNA amplification reactions were carried out using the oligonucleotide sequences listed in Table 3, as the first, second and third oligonucleotides. Solutions were prepared so that the combinations of the cleavage oligonucleotide, and the first and second oligonucleotides would be those as listed in Table 3.

(4) After incubating the above reaction solutions for 5 minutes at 41° C., 4.2 μl of an enzyme solution having the following composition was added.

Composition of Enzyme Solution (each figure represents the amount in a final reaction solution volume of 30 μl)

1.7% sorbitol
    3 μg bovine serum albumin
    142 U T7 RNA polymerase (Gibco)
    8 U AMV-Reverse Transcriptase (Takara Shuzo Co. Ltd.)
    Distilled water for adjusting volume (5) Subsequently, the PCR tubes were incubated at 41° C. for 30 minutes. In order to identify the RNA amplified portion after the reaction, agarose gel (agarose concentration 4%) electrophoresis was performed. Dyeing following the electrophoresis was performed with SYBR Green II (Takara Shuzo Co. Ltd.). When an oligonucleotide probe binds to the specific portion of the target RNA, the RNA portion between the first and second oligonucleotide is amplified and, thereby, a characteristic band could be observed.

Figure 3:
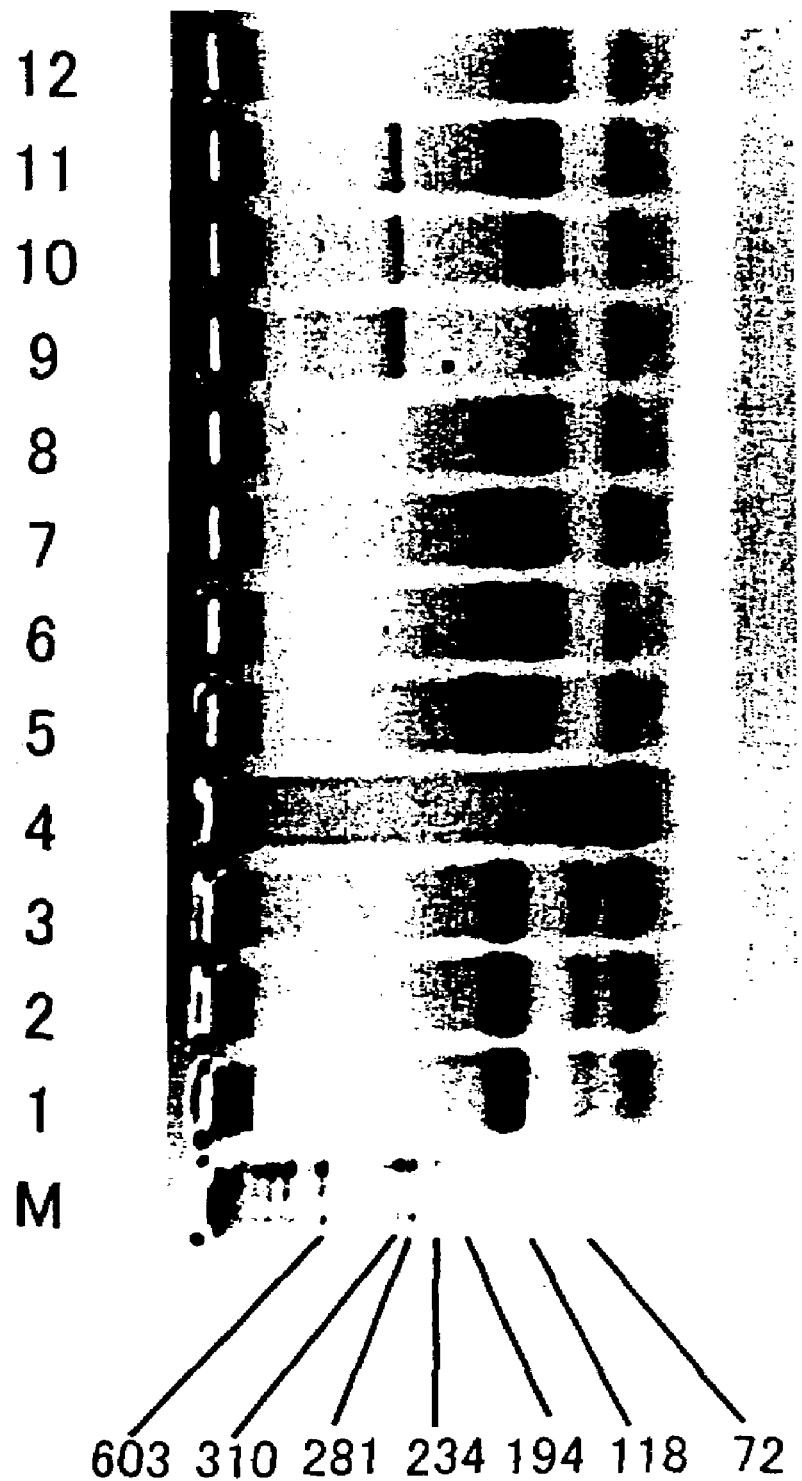
FIG. 3 is a 4% agarose gel electrophoresis diagram for RNA amplification reactions of VT1 RNA standard performed as described in Example 3 using oligonucleotide probe combinations (a) to (c) shown in Table 3 (black and white inverted), with an initial RNA amount of $10_4$ copies/30 µl and $10_3$ copies/30 µl. Lane 1 is the result for combination (a) with an initial RNA amount of $10_4$ copies/30 µl; lanes 2 and 3 are for combination (a) with an initial RNA amount of $10_3$ copies/30 µl; lane 4 is for combination (a) using only the diluent instead of RNA samples (control); lane 5 is the result for combination (b) with an initial RNA amount of $10_4$ copies/30 µl; lanes 6 and 7 are for combination (b) with an initial RNA amount of $10_3$ copies/30 µl; lane 8 is for combination (b) using only the diluent instead of RNA samples (control); lane 9 is the result for combination (c) with an initial RNA amount of $10_4$ copies/30 µl; lanes 10 and 11 are for combination (c) with an initial RNA amount of $10_3$ copies/30 µl; and lane 12 is for combination (c) using only the diluent instead of RNA samples (control). Specific bands were confirmed in every combination.
Figure 4:
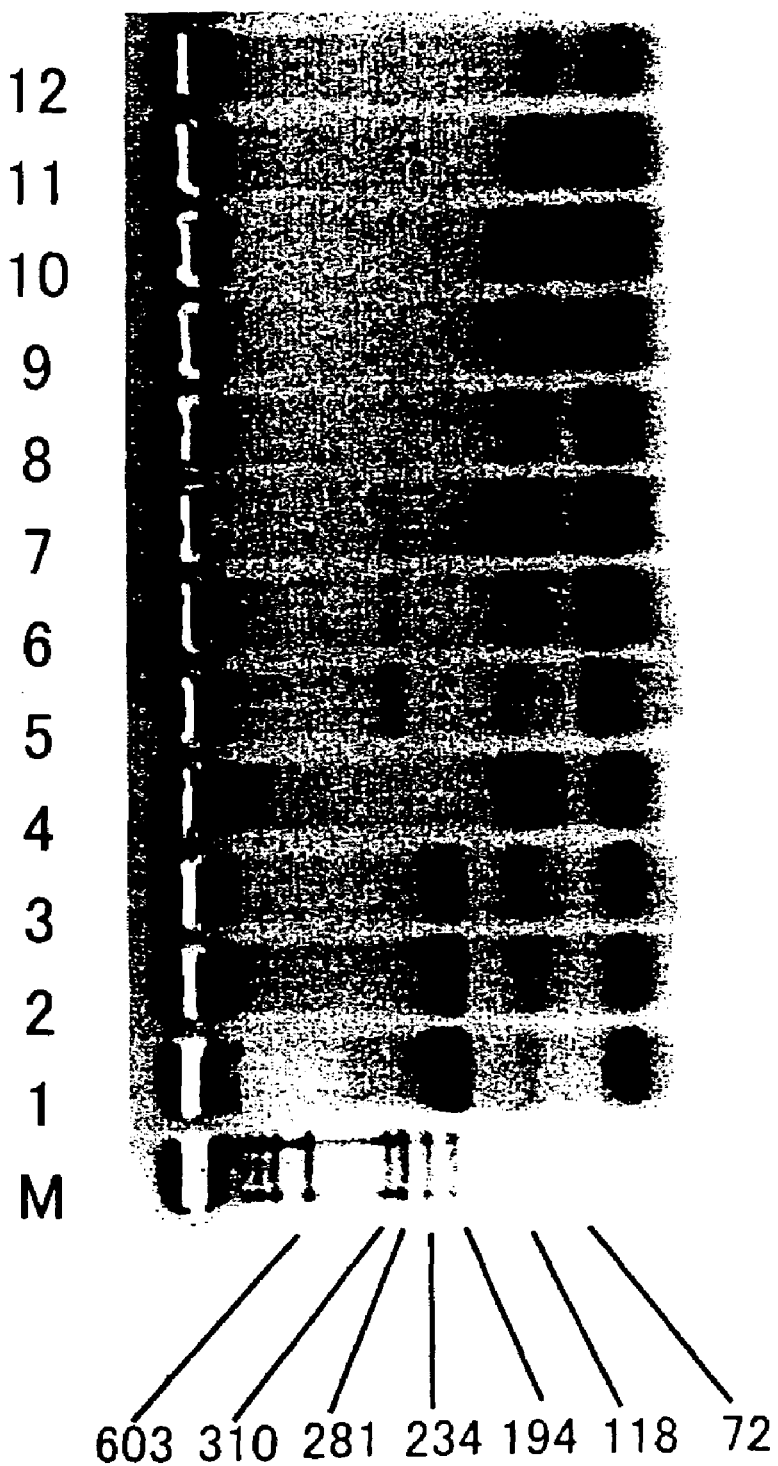
FIG. 4 is a 4% agarose gel electrophoresis diagram for RNA amplification reactions of VT1 RNA standard performed as described in Example 3 using oligonucleotide probe combinations (d) to (f) shown in Table 3 (black and white inverted), with an initial RNA amount of $10_4$ copies/30 µl and $10_3$ copies/30 µl. Lane 1 is the result for combination (d) with an initial RNA amount of $10_4$ copies/30 µl; lanes 2 and 3 are for combination (d) with an initial RNA amount of $10_3$ copies/30 µl; lane 4 is for combination (d) using only the diluent instead of RNA samples (control); lane 5 is the result for combination (e) with an initial RNA amount of $10_4$ copies/30 µl; lanes 6 and 7 are for combination (e) with an initial RNA amount of $10_3$ copies/30 µl; lane 8 is for combination (e) using only the diluent instead of RNA samples (control); lane 9 is the result for combination (f) with an initial RNA amount of $10_4$ copies/30 µl; lanes 10 and 11 are for combination (f) with an initial RNA amount of $10_3$ copies/30 µl; and lane 12 is for combination (f) using only the diluent instead of RNA samples (control). Specific bands were confirmed in every combination.

The results of the electrophoresis are shown in FIGS. 3 and 4 (black and white inverted). The lengths of the specific bands amplified in this reaction are shown in Table 3. Since specific bands were confirmed in any of the combinations shown in Table 3, it was demonstrated that these oligonucleotides are effective in detecting VT1 RNA.

TABLE 3

| Combi-nation | Cleavage Oligo-nucleotide | $2^{nd}$ Oligo-nucleotide Probe | 1st Oligo-nucleotide Probe | Amplification Product Length (Base) |
|---|---|---|---|---|
| (a) | 5S | 5F | 6R | 141 |
| (b) | 6S | 6F | 7R | 166 |
| (c) | 6S | 6F | 8R | 346 |
| (d) | 7S | 7F | 8R | 191 |
| (e) | 7S | 7F | 9R | 281 |
| (f) | 8S | 8F | 9R | 101 |

Table 3 shows the combinations of the cleavage oligonucleotide and the first and second oligonucleotides used in this example, as well as the chain lengths of the amplified specific bands resulted from the RNA amplification reaction using these combinations. The 3' end hydroxyl group of each cleavage oligonucleotide base sequence was aminated. In each second oligonucleotide base sequence, the region of the 1st "A" to the 22nd "A" from the 5' end corresponds to the T7 promoter region, and the subsequent region from the 23rd "G" to the 28th "A" corresponds to the enhancer sequence.

Cleavage oligonucleotide
    5S (SEQ. ID. No. 27)
    6S (SEQ. ID. No. 28)
    7S (SEQ. ID. No. 29)
    8S (SEQ. ID. No. 30)

Second oligonucleotide
    5F (SEQ. ID. No. 36)
    6F (SEQ. ID. No. 37)
    7F (SEQ. ID. No. 38)
    8F (SEQ. ID. No. 39)

First oligonucleotide
    6R (SEQ. ID. No. 2)
    7R (SEQ. ID. No. 26)
    8R (SEQ. ID. No. 3)
    9R (SEQ. ID. No. 4)

Example 4

RNA amplification reactions were carried out using the oligonucleotides which specifically bind to VT2 RNA.

(1) As described in example 2, VT2 standard RNA was diluted to $10_4$ copies/2.5 μl and $10_3$ copies/2.5 μl with an RNA diluent (10 mM Tris-HCl (pH 8.0), 1 mM EDTA, 0.5 U/μl RNase Inhibitor (Takara Shuzo Co. Ltd.), 5 mM DTT). In the control test sections (negative), only the diluent was used.

(2) 23.3 μl of a solution having the following composition was dispensed into 0.5 ml volume PCR tubes (Gene Amp Thin-walled Reaction Tube™, Perkin-Elmer Co. Ltd.), followed by addition of 2.5 μl of the above RNA sample.

Reaction Solution Composition (each concentration represents a concentration in a final reaction solution volume of 30 μl)

60 mM Tris-HCl buffer (pH 8.6)
    17 mM magnesium chloride
    90 mM potassium chloride
    39 U RNase Inhibitor
    1 mM DTT
    0.25 μl of each DATP, dCTP, dGTP, dTTP
    3.6 mM ITP
    3.0 μl of each ATP, CTP, GTP, UTP
    0.16 μM cleavage oligonucleotide
    1.0 μM second oligonucleotide
    1.0 μM first oligonucleotide
    13% DMSO
    Distilled water for adjusting volume (3) RNA amplification reactions were carried out using the oligonucleotide sequences listed in Table 4, as the cleavage oligonucleotide, first and second oligonucleotides. Solutions were prepared so that the combinations of the cleavage oligonucleotide, first and second oligonucleotides would be those as listed in Table 4.

(4) After incubating the above reaction solutions for 5 minutes at 41° C., 4.2 μl of an enzyme solution having the following composition was added.

Composition of Enzyme Solution (each figure represents the amount in a final reaction solution volume of 30 μl)

1.7% sorbitol
    3 μg bovine serum albumin
    142 U T7 RNA polymerase (Gibco)
    8 U AMV-Reverse Transcriptase (Takara Shuzo Co. Ltd.)
    Distilled water for adjusting volume (5) Subsequently, the PCR tubes were incubated at 41° C. for 30 minutes. In order to identify the RNA amplified portion after the reaction, agarose gel (agarose concentration 4%)

electrophoresis was performed. Dyeing following the electrophoresis was performed with SYBR Green II (Takara Shuzo Co. Ltd.). When an oligonucleotide probe binds to the specific portion of the target RNA, the RNA portion between the second and first oligonucleotide is amplified, thereby a characteristic band could be observed.

Figure 5:
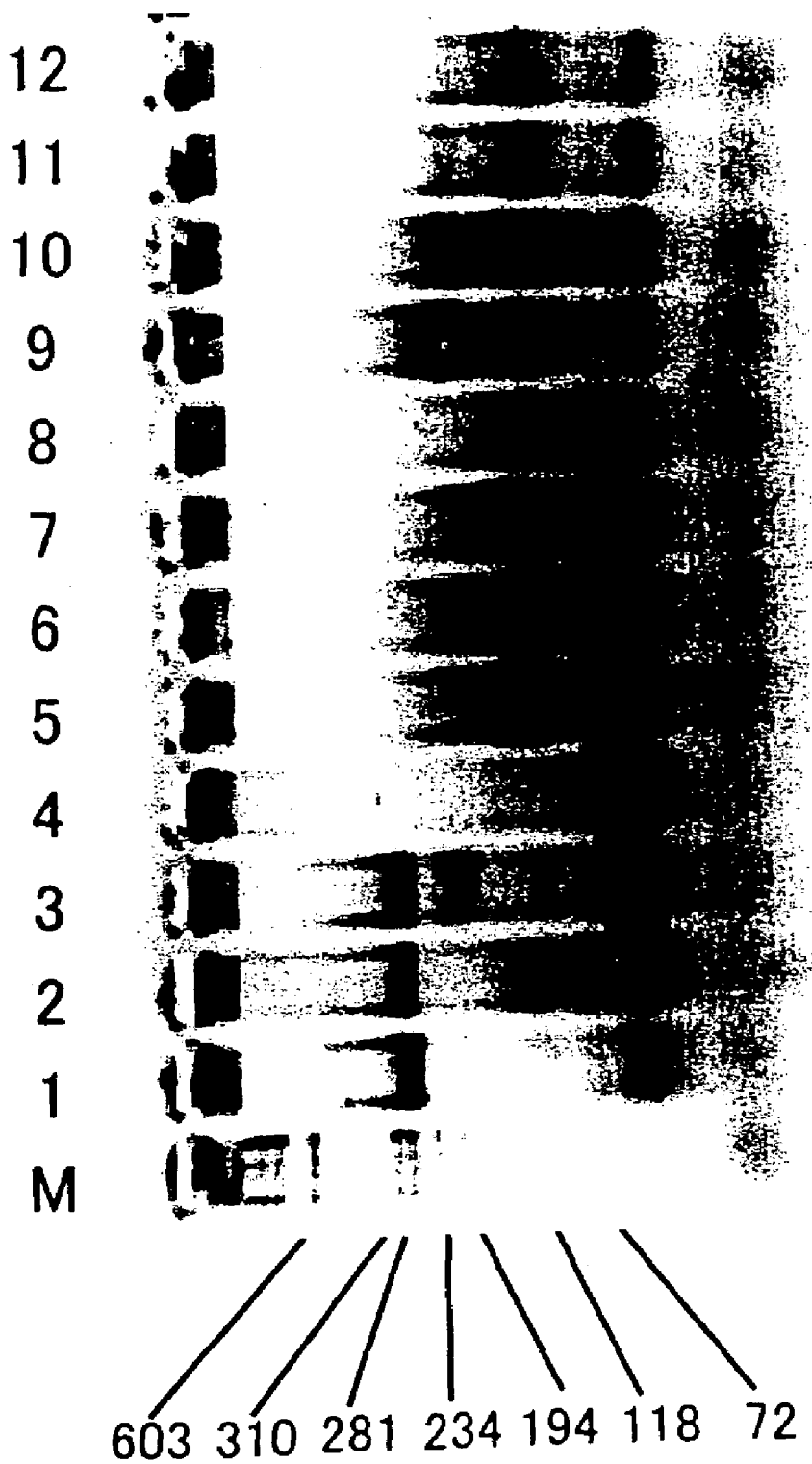
FIG. 5 is a 4% agarose gel electrophoresis diagram for RNA amplification reactions of VT2 RNA standard performed as described in Example 4 using oligonucleotide probe combinations (g) to (i) shown in Table 4 (black and white inverted), with an initial RNA amount of $10_4$ copies/30 µl and $10_3$ copies/30 µl. Lane 1 is the result for combination (g) with an initial RNA amount of $10_4$ copies/30 µl; lanes 2 and 3 are for combination (g) with an initial RNA amount of $10_3$ copies/30 µl; lane 4 is for combination (g) using only the diluent instead of RNA samples (control); lane 5 is the result for combination (h) with an initial RNA amount of $10_4$ copies/30 µl; lanes 6 and 7 are for combination (h) with an initial RNA amount of $10_3$ copies/30 µl; lane 8 is for combination (h) using only the diluent instead of RNA samples (control); lane 9 is the result for combination (i) with an initial RNA/amount of $10_4$ copies/30 µl; lanes 10 and 11 are for combination (i) with an initial RNA amount of $10_3$ copies/30 µl; and lane 12 is for combination (i) using only the diluent instead of RNA samples (control). Specific bands were confirmed in every combination.
Figure 6:
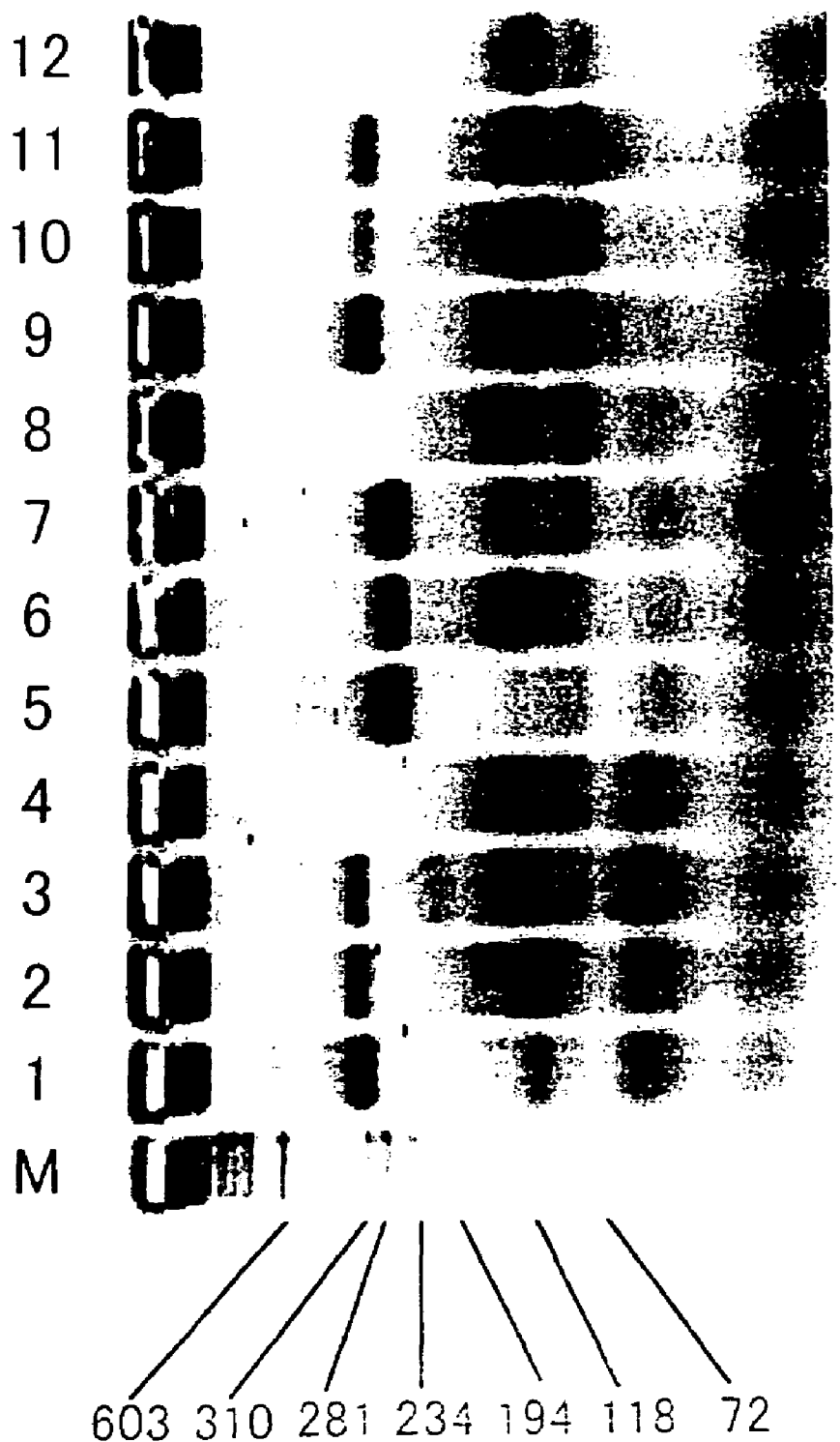
FIG. 6 is a 4% agarose gel electrophoresis diagram for RNA amplification reactions of VT2 RNA standard performed as described in Example 4 using oligonucleotide probe combinations (j) to (l) shown in Table 4 (black and white inverted), with an initial RNA amount of $10_4$ copies/30 µl and $10_3$ copies/30 µl. Lane 1 is the result for combination (j) with an initial RNA amount of $10_4$ copies/30 µl; lanes 2 and 3 are for combination (j) with an initial RNA amount of $10_3$ copies/30 µl; lane 4 is for combination (j) using only the diluent instead of RNA samples (control); lane 5 is the result for combination (k) with an initial RNA amount of $10_4$ copies/30 µl; lanes 6 and 7 are for combination (k) with an initial RNA amount of $10_3$ copies/30 µl; lane 8 is for combination (k) using only the diluent instead of RNA samples (control); lane 9 is the result for combination (l) with an initial RNA amount of $10_4$ copies/30 µl; lanes 10 and 11 are for combination (l) with an initial RNA amount of $10_3$ copies/30 µl; and lane 12 is for combination (l) using only the diluent instead of RNA samples (control). Specific bands were confirmed in every combination.
Figure 7:
FIG. 7 is a 4% agarose gel electrophoresis diagram for RNA amplification reactions of VT2 RNA standard performed as described in Example 4 using oligonucleotide probe combination (m) shown in Table 4 (black and white inverted), with an initial RNA amount of $10_4$ copies/30 µl and $10_3$ copies/30 µl. Lane 1 is the result with an initial RNA amount of $10_4$ copies/30 µl; lanes 2 and 3 are the results with an initial RNA amount of $10_3$ copies/30 µl; and lane 4 is the result obtained by using only the diluent instead of RNA samples (control). Specific bands were confirmed in every combination.

The results of the electrophoresis are shown in FIGS. 5 to 7 (black and white inverted). The lengths of the specific bands amplified in this reaction are shown in Table 4. Since specific bands were confirmed in any of the combinations shown in Table 4, it was demonstrated that these oligonucleotides are effective in detecting VT1 RNA.

TABLE 4

| Combination | Cleavage Oligo-nucleotide | $2^{nd}$ Oligo-nucleotide Probe | 1st Oligo-nucleotide Probe | Amplification Product Length (Base) |
|---|---|---|---|---|
| (g) | B2S | B2F | B4R | 274 |
| (h) | B3S | B3F | B4R | 116 |
| (i) | B3S | B3F | B5R | 187 |
| (j) | B4S | B4F | B7R | 321 |
| (k) | B5S | B5F | B7R | 250 |
| (l) | B5S | B5F | B8R | 298 |
| (m) | B7S | B7F | B9R | 123 |

Table 4 shows the combinations of cleavage, first and second oligonucleotides used in this example, as well as the chain lengths of the amplified specific bands resulted from the RNA amplification reaction using these combinations. The 3' end hydroxyl group of each first oligonucleotide base sequence was aminated. In each second oligonucleotide base sequence, the region of the 1st "A" to the 22nd "A" from the 5' end corresponds to the T7 promoter region, and the subsequent region from the 23rd "G" to the 28th "A" corresponds to the enhancer sequence.

Cleavage oligonucleotide
B2S (SEQ. ID. No. 31)
B3S (SEQ. ID. No. 32)
B4S (SEQ. ID. No. 33)
B5S (SEQ. ID. No. 34)
B7S (SEQ. ID. No. 35)
Second oligonucleotide
B2F (SEQ. ID. No. 40)
B3F (SEQ. ID. No. 41)
B4F (SEQ. ID. No. 42)
B5F (SEQ. ID. No. 43)
B7F (SEQ. ID. No. 44)
First oligonucleotide
B4R (SEQ. ID. No. 8)
B5R (SEQ. ID. No. 9)
B7R (SEQ. ID. No. 10)
B8R (SEQ. ID. No. 11)
B9R (SEQ. ID. No. 12)

Example 5

Combinations of oligonucleotide primers according to the present invention were used for specific detection of different initial copy numbers of the target VT2 RNA.

(1) As described in example 2, VT2 standard RNA was diluted with an RNA diluent (10 mM Tris-HCl (pH 8.0), 1 mM EDTA, 0.5 U/μl RNase Inhibitor (Takara Shuzo Co. Ltd.), 5 mM DTT) to concentrations ranging from $10_5$ copies/2.5 μl to $10_1$ copies/2.5 μl. In the control testing sections, only the diluent was used (Negative).

(2) 23.3 μl of a reaction solution having the composition shown below was dispended into 0.5 ml volume PCR tubes (Gene Amp Thin-walled Reaction Tube™, Perkin-Elmer) followed by addition of 2.5 μl of the above RNA sample.

Reaction Solution Composition (each concentration represents that in a final reaction solution of 30 μl)
60 mM Tris-HCl buffer (pH 8.6)
17 mM magnesium chloride
150 mM potassium chloride
39 U RNase Inhibitor
1 mM DTT
0.25 mM each of dATP, dCTP, dGTP and dTTP
3.6 mM ITP
3.0 mM each of ATP, CTP, GTP and UTP
0.16 μM cleavage oligonucleotide (5S shown in Table 4, wherein its 3' end is aminated)
1.0 μM second oligonucleotide (5F shown in Table 4)
1.0 μM first oligonucleotide (7R shown in Table 4)
25 nM intercalator fluorescent pigment-labeled oligonucleotide (SEQ. ID. No. 25, labeled with an intercalator fluorescent pigment at the phosphorous atom between the 12th "T" and the 13th "A" from the 5' end, and modified with a glycol group at its 3' end hydroxyl)
13% DMSO
Distilled water for adjusting volume (3) After incubating the above reaction solution for 5 minutes at 41° C., 4.2 μl of an enzyme solution having the following composition and pre-incubated for 2 minutes at 41° C. was added.

Enzyme Solution Composition (each concentration represents that in a final reaction solution of 30 μl)
1.7% sorbitol
3 μg bovine serum albumin
142 U T7 RNA polymerase (Gibco)
8 U AMV-Reverse Transcriptase (Takara Shuzo Co. Ltd.)
Distilled water for adjusting volume (4) The PCR tube was then incubated at 41° C. using a direct-measuring fluorescence spectrophotometer equipped with a temperature-controller, and the reaction solution was periodically measured at an excitation wavelength of 470 nm and a fluorescent wavelength of 510 nm.

FIG. 8(A) shows the time-course changes in the fluorescence increase ratio (fluorescence intensity at predetermined time/background fluorescence intensity) of the sample, where enzyme was added at 0 minutes. FIG. 8(B) shows the relationship between the logarithm of the initial RNA amount and the rise time (time at which the relative fluorescence reaches the negative sample's average value plus 3 standard deviations; i.e., the time to reach a ratio of 1.2). The initial RNA amount was between $10_1$ copies/test and $10_5$ copies/test.

FIG. 8 shows that $10_1$ copies were detected at approximately 20 minutes. A fluorescent profile and calibration curve depending on the initial concentration of the labeled RNA were obtained, indicating that it is possible to quantify the VT2 RNA present in unknown samples. This demonstrated that speedy, highly sensitive detection of VT2 RNA is possible using this method.

As explained above, the oligonucleotide provided by the present invention complementarily binds to the intramolecular structure-free region of VT1 RNA or VT2 RNA. By using this oligonucleotide, it is possible to detect an RNA by a process carried out under a relatively low and constant temperature, without the need of an operation which destroys the intramolecular structure of an RNA by heat-degradation so as to improve the primer binding efficiency. As a result, by use of the oligonucleotide according to the present invention, it would be possible to provide an RNA detection method which is speedy, simple, and even suitable for automation.

It will be appreciated by those skilled in the art that while the invention has been described above in connection with particular embodiments and examples, the invention is not necessarily so limited and that numerous other embodiments, examples, uses, modifications and departures from the embodiments, examples and use may be made without departing from the inventive scope of this application.

What is claimed is:

1. A method of detecting VT1 RNA comprising conducting NASBA (nucleic acid sequence-based amplification) or 3SR (self sustained sequence replication) on a sample suspected of containing VT1 RNA using the following primers:

a first oligonucleotide consisting of SEQ ID NO: 2; and a second oligonucleotide consisting of SEQ ID NO: 15 and a RNA polymerase promoter sequence;

which comprises:

contacting VT1 RNA in a buffer suitable for nucleic acid amplification with a first oligonucleotide consisting of SEQ ID NO: 2, a second oligonucleotide consisting of SEQ ID NO: 15 and an RNA polymerase promoter, a cleavage oligonucleotide consisting of 5S (SEQ ID NO: 27) which may be chemically modified or aminated at its 3' end, T7 RNA polymerase, and AMV-reverse transcriptase; and detecting amplified nucleic acids;

wherein the presence or amount of amplified nucleic acids is indicative of the presence of VT1 RNA in said sample.

2. The method of claim 1, which comprises conducting NASBA (nucleic acid sequence-based amplification).

3. The method of claim 1, which comprises conducting 3SR (self sustained sequence replication).

* * * * *

SEQUENCE LISTING

<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
aaaaaacatt atttgtcctg                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
tggcgattta tctgcatccc                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
gatgatgaca attcagtatt                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
ttttattgtg cgtaatccca                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
taatagttct gcgcatcaga                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

```
<400> SEQUENCE: 6
tatacaggtg ttccttttgg                                          20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
tatatgttca agaggggtcg                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
atggtcaaaa cgcgcctgat                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
tagaaagtat ttgttgccgt                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
gtaaggcttc tgctgtgaca                                          20

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
cagtttcaga cagtgcctga                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
ttgctgattc gcccccagtt                                          20

<210> SEQ ID NO 13
<211> LENGTH: 20
```

<212> TYPE: DNA
<213> ORGANISM: Artificial Sequence
<220> FEATURE:
<223> OTHER INFORMATION: Synthetic DNA

<400> SEQUENCE: 13
attattaaag gatattctcc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
attgtttatt tttataacag                                              20

<210> SEQ ID NO 15
<211> LENGTH: 25
<212> TYPE: DNA
<213> ORGANISM: Artificial Sequence
<220> FEATURE:
<223> OTHER INFORMATION: Synthetic DNA

<400> SEQUENCE: 15
tttttatcgc tttgctgatt tttca                                        25

<210> SEQ ID NO 16
<211> LENGTH: 25
<212> TYPE: DNA
<213> ORGANISM: Artificial Sequence
<220> FEATURE:
<223> OTHER INFORMATION: Synthetic DNA

<400> SEQUENCE: 16
cgccattcgt tgactacttc ttatc                                        25

<210> SEQ ID NO 17
<211> LENGTH: 25
<212> TYPE: DNA
<213> ORGANISM: Artificial Sequence
<220> FEATURE:
<223> OTHER INFORMATION: Synthetic DNA

<400> SEQUENCE: 17
tgatctcagt gggcgttctt atgta                                        25

<210> SEQ ID NO 18
<211> LENGTH: 25
<212> TYPE: DNA
<213> ORGANISM: Artificial Sequence
<220> FEATURE:
<223> OTHER INFORMATION: Synthetic DNA

<400> SEQUENCE: 18
tcatcatgca tcgcgagttg ccaga                                        25

<210> SEQ ID NO 19
<211> LENGTH: 25
<212> TYPE: DNA
<213> ORGANISM: Artificial Sequence
<220> FEATURE:
<223> OTHER INFORMATION: Synthetic DNA

<400> SEQUENCE: 19

-continued gtatatgaag tgtatattat ttaaa 25

<210> SEQ ID NO 20
<211> LENGTH: 25
<212> TYPE: DNA
<213> ORGANISM: Artificial Sequence
<220> FEATURE:
<223> OTHER INFORMATION: Synthetic DNA

<400> SEQUENCE: 20
atatatctca ggggaccaca tcggt 25

<210> SEQ ID NO 21
<211> LENGTH: 25
<212> TYPE: DNA
<213> ORGANISM: Artificial Sequence
<220> FEATURE:
<223> OTHER INFORMATION: Synthetic DNA

<400> SEQUENCE: 21
accatcttcg tctgattatt gagca 25

<210> SEQ ID NO 22
<211> LENGTH: 25
<212> TYPE: DNA
<213> ORGANISM: Artificial Sequence
<220> FEATURE:
<223> OTHER INFORMATION: Synthetic DNA

<400> SEQUENCE: 22
ttctaccgtt tttcagattt tacac 25

<210> SEQ ID NO 23
<211> LENGTH: 25
<212> TYPE: DNA
<213> ORGANISM: Artificial Sequence
<220> FEATURE:
<223> OTHER INFORMATION: Synthetic DNA

<400> SEQUENCE: 23
cttacgcttc aggcagatac agaga 25

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA

<400> SEQUENCE: 24
tgtaacgtgg tatagctact 20

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA

<400> SEQUENCE: 25
ttaacgccag atatgatgaa 20

<210> SEQ ID NO 26
<211> LENGTH: 20
<212> TYPE: DNA
<213> ORGANISM: Artificial Sequence

```
<220> FEATURE:
<223> OTHER INFORMATION: Synthetic DNA

<400> SEQUENCE: 26
gatcatccag tgttgtacga                                               20

<210> SEQ ID NO 27
<211> LENGTH: 39
<212> TYPE: DNA
<213> ORGANISM: Artificial Sequence
<220> FEATURE:
<223> OTHER INFORMATION: Synthetic DNA

<400> SEQUENCE: 27
aaaaaacatt atttgtcctg ttaacaaatc ctgtcacat                          39

<210> SEQ ID NO 28
<211> LENGTH: 39
<212> TYPE: DNA
<213> ORGANISM: Artificial Sequence
<220> FEATURE:
<223> OTHER INFORMATION: Synthetic DNA

<400> SEQUENCE: 28
tggcgattta tctgcatccc cgtacgactg atccctgca                          39

<210> SEQ ID NO 29
<211> LENGTH: 39
<212> TYPE: DNA
<213> ORGANISM: Artificial Sequence
<220> FEATURE:
<223> OTHER INFORMATION: Synthetic DNA

<400> SEQUENCE: 29
gatcatccag tgttgtacga aatccctct gtatttgcc                           39

<210> SEQ ID NO 30
<211> LENGTH: 39
<212> TYPE: DNA
<213> ORGANISM: Artificial Sequence
<220> FEATURE:
<223> OTHER INFORMATION: Synthetic DNA

<400> SEQUENCE: 30
gatgatgaca attcagtatt aatgccacgc ttcccagaa                          39

<210> SEQ ID NO 31
<211> LENGTH: 39
<212> TYPE: DNA
<213> ORGANISM: Artificial Sequence
<220> FEATURE:
<223> OTHER INFORMATION: Synthetic DNA

<400> SEQUENCE: 31
tatacaggtg ttcctttggg ctgaagtaat cagcaccag                          39

<210> SEQ ID NO 32
<211> LENGTH: 39
<212> TYPE: DNA
<213> ORGANISM: Artificial Sequence
<220> FEATURE:
<223> OTHER INFORMATION: Synthetic DNA

<400> SEQUENCE: 32
tatatgttca agagggtcg atatctctgt ccgtatact                           39
```

<210> SEQ ID NO 33
<211> LENGTH: 39
<212> TYPE: DNA
<213> ORGANISM: Artificial Sequence
<220> FEATURE:
<223> OTHER INFORMATION: Synthetic DNA

<400> SEQUENCE: 33
atggtcaaaa cgcgcctgat agacatcaag ccctcgtat            39

<210> SEQ ID NO 34
<211> LENGTH: 39
<212> TYPE: DNA
<213> ORGANISM: Artificial Sequence
<220> FEATURE:
<223> OTHER INFORMATION: Synthetic DNA

<400> SEQUENCE: 34
tagaaagtat tgttgccgt attaacgaac ccggccaca             39

<210> SEQ ID NO 35
<211> LENGTH: 39
<212> TYPE: DNA
<213> ORGANISM: Artificial Sequence
<220> FEATURE:
<223> OTHER INFORMATION: Synthetic DNA

<400> SEQUENCE: 35
gtaaggcttc tgctgtgaca gtgacaaaac gcagaactg            39

<210> SEQ ID NO 36
<211> LENGTH: 53
<212> TYPE: DNA
<213> ORGANISM: Artificial Sequence
<220> FEATURE:
<223> OTHER INFORMATION: Synthetic DNA

<400> SEQUENCE: 36
aattctaata cgactcacta tagggagatt tttatcgctt tgctgatttt tca            53

<210> SEQ ID NO 37
<211> LENGTH: 53
<212> TYPE: DNA
<213> ORGANISM: Artificial Sequence
<220> FEATURE:
<223> OTHER INFORMATION: Synthetic DNA

<400> SEQUENCE: 37
aattctaata cgactcacta tagggagacg ccattcgttg actacttctt atc            53

<210> SEQ ID NO 38
<211> LENGTH: 53
<212> TYPE: DNA
<213> ORGANISM: Artificial Sequence
<220> FEATURE:
<223> OTHER INFORMATION: Synthetic DNA

<400> SEQUENCE: 38
aattctaata cgactcacta tagggagatg atctcagtgg gcgttcttat gta            53

<210> SEQ ID NO 39
<211> LENGTH: 53
<212> TYPE: DNA
<213> ORGANISM: Artificial Sequence
<210> SEQ ID NO 39
<211> LENGTH: 53
<212> TYPE: DNA
<213> ORGANISM: Artificial Sequence
<220> FEATURE:
<223> OTHER INFORMATION: Synthetic DNA

<400> SEQUENCE: 39
aattctaata cgactcacta tagggagatc atcatgcatc gcgagttgcc aga    53

<210> SEQ ID NO 40
<211> LENGTH: 53
<212> TYPE: DNA
<213> ORGANISM: Artificial Sequence
<220> FEATURE:
<223> OTHER INFORMATION: Synthetic DNA

<400> SEQUENCE: 40
aattctaata cgactcacta tagggagagt atatgaagtg tatattattt aaa    53

<210> SEQ ID NO 41
<211> LENGTH: 53
<212> TYPE: DNA
<213> ORGANISM: Artificial Sequence
<220> FEATURE:
<223> OTHER INFORMATION: Synthetic DNA

<400> SEQUENCE: 41
aattctaata cgactcacta tagggagaat atatctcagg ggaccacatc ggt    53

<210> SEQ ID NO 42
<211> LENGTH: 53
<212> TYPE: DNA
<213> ORGANISM: Artificial Sequence
<220> FEATURE:
<223> OTHER INFORMATION: Synthetic DNA

<400> SEQUENCE: 42
aattctaata cgactcacta tagggagaac catcttcgtc tgattattga gca    53

<210> SEQ ID NO 43
<211> LENGTH: 53
<212> TYPE: DNA
<213> ORGANISM: Artificial Sequence
<220> FEATURE:
<223> OTHER INFORMATION: Synthetic DNA

<400> SEQUENCE: 43
aattctaata cgactcacta tagggagatt ctaccgtttt tcagatttta cac    53

<210> SEQ ID NO 44
<211> LENGTH: 53
<212> TYPE: DNA
<213> ORGANISM: Artificial Sequence
<220> FEATURE:
<223> OTHER INFORMATION: Synthetic DNA

<400> SEQUENCE: 44
aattctaata cgactcacta tagggagact tacgcttcag gcagatacag aga    53